US00PP08226P

United States Patent [19]

VandenBerg

[11] Patent Number: Plant 8,226

[45] Date of Patent: May 11, 1993

[54] CHRYSANTHEMUM PLANT NAMED YELLOW BRIOSO

[75] Inventor: Cornelis P. VandenBerg, Salinas, Calif.

[73] Assignee: Yoder Brothers, Inc., Barberton, Ohio

[21] Appl. No.: 701,087

[22] Filed: May 16, 1991

[51] Int. Cl.[5] ..... A01H 5/00

[52] U.S. Cl. ..... Plt./82.2

[58] Field of Search ..... Plt./74.1, 82.2

[56] References Cited

U.S. PATENT DOCUMENTS

| | | | |
|---|---|---|---|
| P.P. 6,095 | 2/1988 | Van der Knaap | Plt. 74 |
| P.P. 6,497 | 12/1988 | VandenBerg | Plt. 74 |
| P.P. 6,740 | 4/1989 | Van der Knaap | Plt. 74 |
| P.P. 6,867 | 6/1989 | Van der Knaap | Plt. 74 |
| 4,616,099 | 10/1986 | Sparkes | 47/58 |

OTHER PUBLICATIONS

Gosling, ed., 1979, "The Chrysanthemum Manual-6th edition", The National Chrysanthemum Society, London, Essex Telegraph Press, Ltd., pp. 329-336.

Broertjes et al., 1978. Application of Mutation Breeding Methods in the Improvement of Vegetatively Propagated Crops, Elsevier Sci Pub Co., New York, pp. 162-175.

Broertjes et al. 1980. "A mutant of a mutant of a mutant of a . . . Irradiation of progressive radiation-induced mutants in a mutation breeding programme with *Chrysanthemum morifolium*", Euphytica 29: 526-530.

Searle, et al. 1968. "Chrysanthemum the Year Round", Blanford Press, London, pp. 27-29, 320-327.

Chan, 1966. "Chrysanthemum and rose mutations induced by X-rays", Am. Soc. Hort. Sci. Proc., pp. 613-620.

Broertjes, 1966, "Mutation breeding of chrysanthemums", Euphytica, 15: 156-162.

Dowrick et al., 1966, "The induction of mutations in Chrysanthemum using X-and gamma radiation", Euphytica, 15:204-210.

*Primary Examiner*—Howard J. Locker

*Attorney, Agent, or Firm*—Foley & Lardner

[57] ABSTRACT

A Chrysanthemum plant named Yellow Brioso particularly characterized by its flat capitulum form; daisy capitulum type; yellow ray floret color; diameter across face of capitulum of 108 to 114 mm when fully opened, when grown as a single stem spray cut mum; photoperiodic flowering response to short days of 52 to 53 days; and plant height, with 7 to 14 long days after planting rooted cuttings prior to start of short days and with no growth regulator applications, ranges from 99 to 102 cm when grown as a single stem cut mum.

1 Drawing Sheet

The present invention comprises a new and distinct cultivar of Chrysanthemum, botanically known as *Dendranthema grandiflora*, and referred to by the cultivar name Yellow Brioso.

Yellow Brioso, identified as 3563 (83-678E09), is a spontaneous mutation found in a selection resulting from a mutation induction program. The new cultivar was discovered and selected by Cornelis P. VandenBerg on Nov. 21, 1988 in a controlled environment in Salinas, Calif., as a spontaneous mutation within a flowering block of a selection (2841) made after irradiating the cultivar identified as Brioso, disclosed in U.S. Plant Pat. No. 6,497, with an x-ray source of 2000 rads in Fort Myers, Fla., in October 1986.

The irradiation program resulting in the selection 2841 had as its primary objective the expansion of color ranges of the parent cultivar Brioso, a daisy cut spray having purple ray floret color. The irradiation program comprised irradiating cuttings of the parent cultivar at irradiation levels of 1500, 1750 and 2000 rads. A total of 593 cuttings harvested from a total of 225 irradiated plants were planted on Feb. 9, Feb. 2, and Jan. 12, 1987, respectively. Of these, 13 initial selections were made, which selections were then revegetated and reflowered. Four consecutive flowerings resulting in discarding 9 of the original 13 selections on Jan. 12, 1988. Three selections were retained as possible introductions, and one selection, 2841, was retained for possible re-irradiation to obtain a yellow mutation of Brioso, which color was not found among the initial selections resulting from irradiating Brioso. The three retained selections will be commercially introduced as Light Brioso, Dark Brioso and Bronze Brioso, all of which are disclosed in pending plant patent applications of applicant. The retained selection 2841 to be re-irradiated was discarded on Jul. 19, 1990, since the yellow sport as herein described as Yellow Brioso was already obtained as a spontaneous mutation within this selection.

The first act of asexual reproduction of Yellow Brioso was accomplished when vegetative cuttings were taken from the initial selection in January 1989 in a controlled environment in Salinas, Calif., by technicians working under supervision of Cornelis P. VandenBerg.

Horticulture examination of controlled flowerings of successive plantings has shown that the unique combination of characteristics as herein disclosed for Yellow Brioso are firmly fixed and are retained through successive generations of asexual reproduction.

Yellow Brioso has not been observed under all possible environmental conditions. The phenotype may vary significantly with variations in environment such as temperature, light intensity and daylength.

The following observations, measurements and comparisons describe plants grown in Salinas, Calif. under greenhouse conditions which approximate those generally used in commercial greenhouse practice. Only two flowerings were evaluated of Yellow Brioso, accounting for the much narrower range of height and response in comparison with the other noted mutations of Brioso, which were selected earlier and thus had evaluations over a longer period of time than Yellow Brioso.

The following traits have been repeatedly observed and are determined to be basic characteristics of Yellow Brioso, which, in combination, distinguish this Chrysanthemum as a new and distinct cultivar:

1. Flat capitulum form.
2. Daisy capitulum type.
3. Yellow ray floret color.
4. Diameter across face of capitulum of 108 to 114 mm when fully opened, when grown as a single stem cut mum.
5. Photoperiodic flowering response to short days of 52 to 53 days.
6. Plant height, with 7 to 14 long days after planting rooted cuttings prior to start of short days and with no growth regulator applications, ranges from 99 to 102 cm when grown as a single stem cut mum.

The accompaning photographic drawing is a view of a single stem of Yellow Brioso, with the colors being as nearly true as possible with illustrations of this type. The precise ray floret color of Yellow Brioso has not been captured in the photograph. The flower typified by the lowest full flower in the center of the photo is more pale yellow, and the peripheral flowers display too much gold. The true color of Yellow Brioso is an intense bright yellow, the color value of which is correctly noted below.

Of the commercial cultivars known to the inventor, the most similar in comparison to Yellow Brioso is the parent cultivar Brioso. All traits of Yellow Brioso are similar to those of Brioso, except for the ray floret color, and plant height. The ray floret color of Yellow Brioso is a bright yellow, while the ray floret color of Brioso is described as purple. In two flowering evaluations the height of Yellow Brioso was described as 5 cm shorter than the height of Brioso.

In the following description color references are made to the Royal Horticultural Society Colour Chart. The color values were determined on plant material grown as a single stem spray cut mum in Salinas, Calif. on Jun. 20, 1990.

Classification:

*Botanical.*—*Dendranthema grandiflora* cv Yellow Brioso.

*Commercial.*—Flat daisy spray cut mum.

INFLORESCENCE

A. Capitulum:

*Form.*—Flat.

*Type.*—Daisy.

*Diameter across face.*—108 to 114 mm when fully opened.

B. Corolla of ray florets:

*Color (general tonality from a distance of three meters).*—Yellow.

*Color (upper surface).*—6B to 6C.

*Color (under surface).*—6C to 6D, slightly overlaid with bronze tinges, closest to 168D to 169A.

*Shape.*—Oblong.

C. Corolla of disc florets:

*Color (mature).*—14A.

*Color (immature).*—144B.

D. Reproductive organs:

*Androecium.*—Present on disc florets only; scant pollen.

*Gynoecium.*—Present on both ray and disc florets.

PLANT

A. General appearance:

*Height.*—99 to 102 cm when grown as a single stem cut mum with 7 to 14 long days after planting rooted cuttings prior to start of short days and no growth regulator applications.

B. Foliage:

*Color (upper surface).*—147A.

*Color (under surface).*—147B.

*Shape.*—Lobed and slightly serrated.

I claim:

1. A new and distinct Chrysanthemum plant named Yellow Brioso, as described and illustrated.

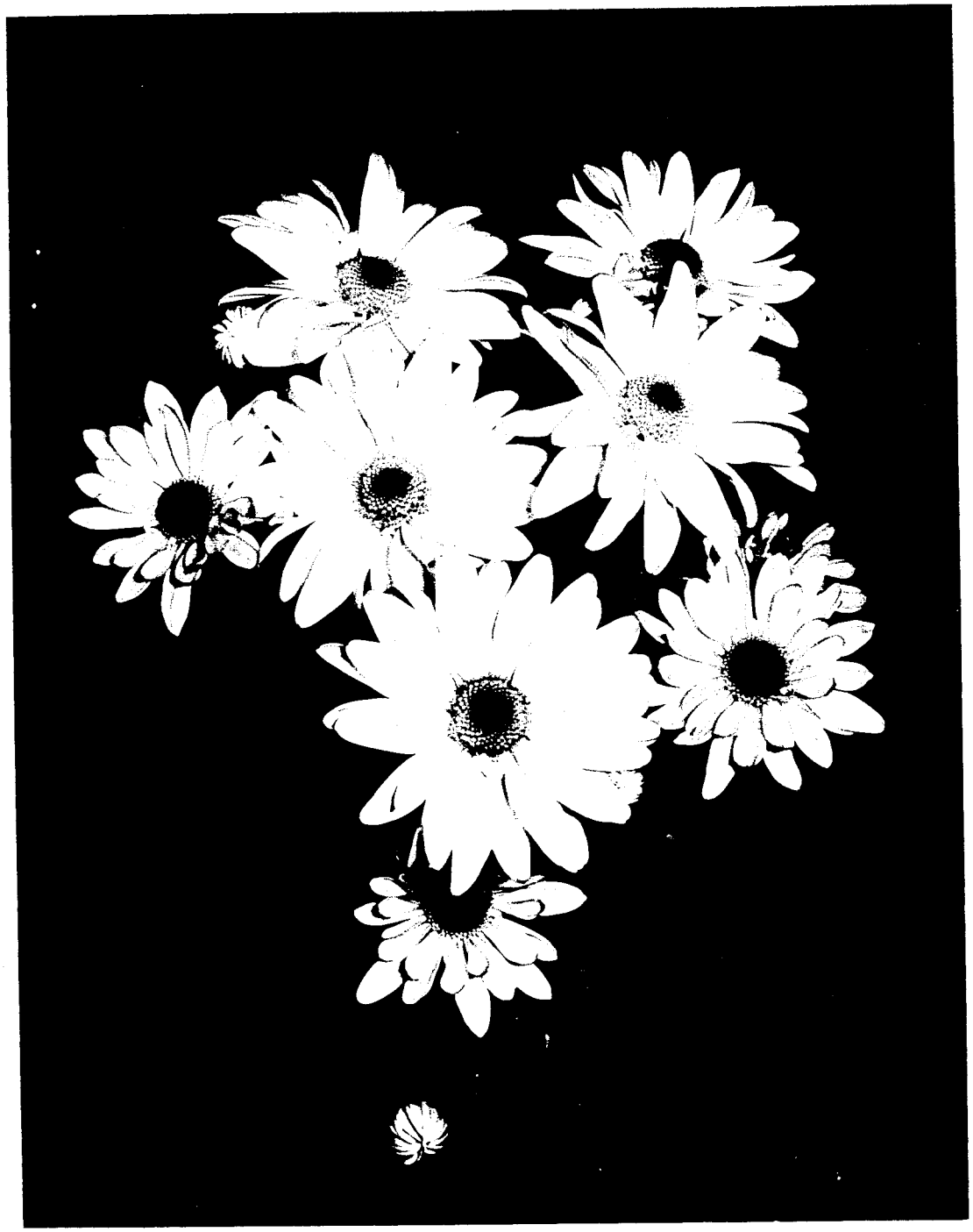

* * * * *